(12) United States Patent  
Lee (10) Patent No.: US 6,372,514 B1  
(45) Date of Patent: Apr. 16, 2002

(54) EVEN FLUID FRONT FOR LIQUID SAMPLE ON TEST STRIP DEVICE

(75) Inventor: Jin Po Lee, Poway, CA (US)

(73) Assignee: Syntron Bioresearch, Inc., Carlsbad, CA (US)

( * ) Notice: Subject to any disclaimer, the term of this patent is extended or adjusted under 35 U.S.C. 154(b) by 0 days.

(21) Appl. No.: 09/157,279

(22) Filed: Sep. 18, 1998

(51) Int. Cl.$^7$ ................ G01N 33/543; G01N 33/558
(52) U.S. Cl. ............... 436/518; 422/56; 422/57; 422/58; 435/5; 435/6; 435/7.1; 435/7.2; 435/7.92; 435/287.2; 435/287.8; 435/805; 435/970; 436/164; 436/169; 436/172; 436/510; 436/514; 436/527; 436/808; 436/810; 436/46; 436/165
(58) Field of Search ............... 435/5, 6, 7, 7.1, 435/7.2, 7.92, 287.2, 287.8, 970, 805; 436/164, 169, 172, 510, 518, 501, 514, 527, 808, 810, 46, 165; 422/58, 57, 56, 52, 104, 100, 99

(56) References Cited

U.S. PATENT DOCUMENTS

| 3,868,219 | A | 2/1975 | Hurenkamp ............... 23/230 |
| 3,884,641 | A | 5/1975 | Kraffczyk et al. ............ 23/253 |
| 4,046,514 | A | 9/1977 | Johnston et al. ............. 23/253 |
| 4,059,407 | A | 11/1977 | Hochstrasser ............... 23/253 |
| 4,168,146 | A | 9/1979 | Grubb et al. ............... 23/230 |
| 4,200,690 | A | 4/1980 | Root et al. ................ 435/7 |
| 4,703,017 | A | 10/1987 | Campbell et al. |
| 4,874,691 | A | 10/1989 | Chandler et al. |
| 4,916,056 | A | 4/1990 | Brown, III et al. |
| 4,943,522 | A | 7/1990 | Eisinger et al. ............. 435/7 |
| 4,956,302 | A | 9/1990 | Gordon et al. ............. 436/161 |
| 5,008,080 | A | 4/1991 | Brown, III et al. ........... 422/56 |
| 5,145,789 | A | 9/1992 | Corti et al. ................ 436/530 |
| 5,149,622 | A | 9/1992 | Brown et al. ................ 435/5 |
| 5,160,701 | A | 11/1992 | Brown, III et al. ........... 422/56 |
| 5,234,813 | A | * 8/1993 | McGeehan et al. |
| 5,384,264 | A | 1/1995 | Chen et al. ................ 436/525 |
| 5,559,041 | A | 9/1996 | Kang et al. ................ 436/518 |
| 5,591,645 | A | 1/1997 | Rosenstein ................ 436/514 |
| 5,602,040 | A | 2/1997 | May et al. ................ 436/514 |
| 5,622,871 | A | 4/1997 | May et al. ................ 436/514 |
| 5,656,503 | A | 8/1997 | May et al. ................ 436/514 |
| 5,714,389 | A | 2/1998 | Charlton et al. ............ 436/514 |
| 5,820,826 | A | 10/1998 | Moorman ................ 422/104 |

FOREIGN PATENT DOCUMENTS

| EP | 0 250 137 B1 | 12/1987 | ......... G01N/33/558 |
| EP | 0 291 194 B1 | 11/1988 | ......... G01N/33/543 |
| EP | 0 296 724 A3 | 12/1988 | ......... G01N/33/558 |
| EP | 0 296 724 A2 | 12/1988 | ......... G01N/33/558 |
| EP | 0 560 410 A2 | 9/1993 | ......... G01N/33/52 |
| EP | 0 582 231 A1 | 2/1994 | ......... G01N/33/558 |
| GB | 2 204 398 B | 11/1988 | |
| WO | 88/08534 | 11/1988 | ......... G01N/33/543 |

* cited by examiner

Primary Examiner—Bao-Thuy L. Nguyen  
(74) Attorney, Agent, or Firm—Campbell & Flores (57) ABSTRACT

Test strip device for accepting a liquid sample and forming an even fluid front across the test strip. When the sample is applied to a contacting surface, it runs down the surface where it collects between the contacting surface and a slope surface. As the sample collects, it evenly reaches fluid flow contact with an absorbent membrane. As a result, the sample forms an even fluid front across the membrane, improving the performance of the test strip device. Methods for using the device to accept a sample and to detect an analyte in the liquid sample are also provided.

14 Claims, 8 Drawing Sheets

EVEN FLUID FRONT FOR LIQUID SAMPLE ON TEST STRIP DEVICE

FIELD OF THE INVENTION

This invention relates to a novel analytical test device for analysis of biological fluids such as urine. The invention further relates to methods for detecting analytes in fluids using the test device.

BACKGROUND INFORMATION

The sampling and testing of biological fluids such as urine for the presence of analytes provide important information regarding various health-related matters, including pregnancy and conception.

In recent years, test devices have undergone nearly continuous refinement in an effort to simplify and speed the process of detecting selected ligand in fluids. As a result of this work, current test devices use an immunoassay for determining pregnancy or conception. In these devices a reagent, such as an antibody, specifically reacts with an analyte to form a complex, which can usually be detected by the unaided eye.

Current pregnancy test devices assay for hormones associated with pregnancy, such as, for example, chorionic gonadotrophin (hereinafter "hCG") since the presence of hCG in urine is usually an indicator that a woman is pregnant. Such test devices obtain qualitative results indicating either the presence or absence of hCG. Typically, a pregnancy immunoassay contains an antibody directed against hCG. The reaction complex can then be viewed by the user.

Conception test devices also assay for hormones associated with the ovarian cycle, such as, for example, luteinizing hormone (hereinafter "LH"). LH is present normally in urine but its concentration increases markedly during ovulation, the time at which a woman is most likely to conceive. Thus, the probability that a woman can conceive a child varies directly with LH concentration. Such test devices obtain semi-quantitative results regarding the relative concentration of LH in the urine. Typically, a conception immunoassay contains an antibody directed against LH and a separate detection antibody.

In known devices, the fluid to be tested wicks up through an absorbent membrane that is in fluid flow contact with the reagents that detect an analyte in a fluid. A major problem with this type of device is that as the fluid progresses through the membrane, the front edge of the fluid is uneven. The uneven fluid front will cause the results to be smeared, produce false negatives and make the results difficult to detect. These artifacts are called "leading edge effects." An uneven fluid front can arise for a variety of reasons, for example, because the sample is not uniformly applied to the absorbent membrane.

Therefore, a need exists for a device that does not produce an uneven fluid front and associated leading edge effects. The present invention provides a device that eliminates the uneven fluid front problem and related methods of using such a device.

SUMMARY OF THE INVENTION

The present invention provides an analytical test device for analyzing biological fluids, for example, urine. The device has a top with one or more display ports, and optionally, a sample aperture, an entry port and a vertical bar. The device also has a bottom with an upper plane, a slope and a contacting surface attached to the slope at a descending angle, optionally, a lower plane between the slope and contacting surface and, optionally, an entry port. The device further has a strip made up of an absorbent membrane, a reaction membrane with one or more reagents that form a reaction complex with an analyte in a fluid sample and, optionally, a collecting pad.

The absorbent membrane, the reaction membrane and the collecting pad, when present, are in fluid flow contact with one other. The strip is placed on the bottom such that the reaction membrane is visible through the display port and the absorbent membrane is on the slope and on the lower plane when present. The fluid sample contacts the absorbent membrane by first contacting the contacting surface when the top and bottom are assembled.

In one embodiment, the analytical test device has the contacting surface extending outward from the bottom. Here the absorbent membrane is in fluid flow contact with the contacting surface through the entry port. The top also has a vertical bar that deflects the absorbent membrane to the follow the contour of the slope.

The present invention also provides methods for detecting an analyte in a fluid sample, comprising contacting the fluid sample to the contacting surface of the analytical test device and detecting the analyte by observing the reaction complex through the display port. In one method the reaction complex is visible.

DETAILED DESCRIPTION OF THE INVENTION

The present invention is directed to an analytical test device that eliminates the uneven fluid front and leading edge effects-associated with prior devices. The device ensures that fluid sample comes into fluid flow contact with the membrane that contains the reagents to detect the analyte, evenly and at the same height across the membrane, thereby producing an even fluid front.

By laying the device flat, the user can simply apply fluid sample to the contacting surface, allowing the fluid sample to run down into the device where the fluid sample gradually builds up until it comes into fluid flow contact with the membrane. Thus, an even fluid front will be formed on the membrane because the fluid sample level rises gradually and contacts the membrane evenly and at the same height across the membrane. Optionally, the user can tilt the device so that when fluid sample is applied to the contacting surface, the fluid sample remains on the contacting surface. After the user decides that a sufficient amount of fluid sample is collected, the device is laid flat so that the fluid sample runs down into the device and comes into fluid flow contact with the membrane evenly and at the same height across the membrane, thereby producing an even fluid front.

A further advantage of the analytical test device is that the user can-control when the assay starts. Thus, if desired, the user can add more than one fluid sample to the contacting surface before laying the device flat. This feature is especially important where the user only wishes to know whether an analyte is present in more than one fluid sample. In prior devices, once the fluid sample is added, the assay proceeds and the reagents are depleted before a second fluid sample can be added. Thus, the user of those devices is not given the time to test additional samples.

The analytical test device of the present invention includes a top and a bottom. The top has a display port that allows the user to see the results. Preferably, the top will have a first display port and a second display port that are in close proximity for easy comparison of results. Optionally, the top will also have a sample aperture. The bottom has an entry port for the fluid sample. Inside the device is a strip formed by an absorbent membrane, a reaction membrane and, optionally, a collecting pad. The absorbent membrane and the reaction membrane contain the reagents to detect an analyte in a fluid sample. When the top is placed on the bottom in the assembled device, the absorbent membrane will be positioned on the bottom toward the entry port and the reaction membrane will be positioned on the bottom underneath the display port.

The bottom is divided into an upper plane and a slope. As used herein, the term "slope" refers to a surface or plane of the bottom of the device that is at such an angle in relation to the other plane or planes of the bottom that it slows the rate of fluid sample wicking through the absorbent membrane. Thus, the slope prevents an excess amount of fluid sample migrating through the absorbent membrane, which would otherwise compromise the assay.

Also, the bottom has a contacting surface attached to the slope at a descending angle. If the top has the optional sample aperture, the contacting surface is inside the assembled top and bottom below the sample aperture. However, if the top does not have the sample aperture, the contacting surface extends outward from the bottom of the device and is indirectly connected to the slope by a lower plane of the bottom. When the lower plane is present, the absorbent membrane will extend along the lower plane and along the slope. Preferably, the contacting surface extending outward from the bottom will be inside a protruding sample well.

Also, the device preferably has a vertical bar extending downward from the top. As used herein, the term "vertical bar" refers to a part of the top of the device extending downward from the top at a point just in front of the slope that holds or deflects the absorbent membrane to follow the contour of the slope. Optionally, the vertical bar can extend downward far enough to only allow fluid sample to proceed further into the device by wicking through the absorbent membrane.

An amount of fluid sample, such as urine, is applied to the contacting surface through the sample aperture or through the protruding sample well. As described above, if desired, more than one fluid sample can be applied or contacted with the contacting surface by tilting the device before adding fluid sample. Tilting the device, therefore, can control the start of the assay.

The fluid sample then proceeds by capillary action (i.e., wicking) through the absorbent membrane. Bound evenly and at the same height extending from side to side of the absorbent membrane at a downstream point spatially separated from where the fluid sample first contacts the absorbent membrane and downstream from the vertical bar, when present, is a diffusively bound labeled reagent. The spatial separation ensures that the fluid sample wicks up through the absorbent membrane to contact the diffusively bound labeled reagent. Thus, the diffusively bound labeled reagent stays within the absorbent membrane and does not migrate into the fluid sample, which would otherwise destroy performance of the assay.

If analyte is present in the fluid sample it will complex with the diffusively bound labeled reagent. The fluid sample containing either diffusively bound labeled reagent alone or a diffusively bound labeled reagent/analyte complex (i.e., "first complex") will move by wicking up to a "test region" in the reaction membrane. Bound evenly and at the same height across the reaction membrane in the test region is a non-diffusively bound reagent capable of complexing the first complex. The non-diffusively bound reagent may be non-diffusively bound to the reaction membrane by means known in the art, including covalent bonding or attachment to an insoluble protein-coated surface (see, for example, U.S. Pat. No. 4,200,690, which is incorporated herein by reference). Preferably, the non-diffusively bound reagent will be bound in a bar shape extending from side to side of the reaction membrane in a manner that is similar to the attachment of the diffusively bound labeled reagent to the absorbent membrane.

If a first complex is present in the fluid sample, the analyte portion of the first complex will bind to the non-diffusively bound reagent creating a detectable signal, preferably a visible straight line or bar extending from side to side of the reaction membrane at the first display port. As a control, the fluid sample will continue its migration along the reaction membrane past the first display port to a "control region" portion of the reaction membrane.

The control region is so called because bound evenly and at the same height extending from side to side of the reaction membrane is a non-diffusively bound control reagent. The diffusively bound labeled reagent, complexed with analyte or not, will bind to the non-diffusively bound control reagent present in the control region. This binding will create a detectable signal, preferably a straight line or bar extending from side to side of the reaction membrane. For ease of comparison, the shape and orientation of the non-diffusively bound control reagent should be similar to the shape and orientation of the non-diffusively bound reagent. In addition, the non-diffusively bound control reagent may be non-diffusively bound in the manner similar to that of the non-diffusively bound reagent, described above. Thus, when the top is aligned with bottom in the assembled device the diffusively bound labeled reagent will be bound on the absorbent membrane near the contacting surface, the non-diffusively bound reagent will be bound beneath first display port and the non-diffusively bound control reagent will be bound beneath second display port.

The results can then be interpreted. If a signal appears at the first display port and a signal appears at the second display port, the test is positive for the presence of analyte. If there is no detectable signal at the first display port compared to the signal at the second display port, the test is negative for the presence of analyte. If there is no signal at the second display port the user is alerted that the test results are compromised and that the test should be repeated.

Alternatively, the analytical test device can employ a competitive assay system. A diffusively bound labeled reagent capable of competing with the analyte for a non-diffusively bound reagent is applied evenly and at the same height extending from side to side of the absorbent membrane. It is positioned at a downstream point spatially separated from the point where the absorbent membrane comes into contact with the fluid sample and downstream from the vertical bar, when present. The diffusively bound labeled reagent here does not complex with the analyte. A non-diffusively bound reagent that can bind either the analyte or the diffusively bound reagent is applied evenly and at the same height extending from side to side of the reaction membrane at a point beneath the display port. In this embodiment of the analytical test device, the top need only have one display port, as no comparison is required. However, if desired, a control region may be incorporated to demonstrate the integrity of the reagents and device. In this embodiment, the presence of a signal, such as a solid straight line or bar across the reaction membrane in the display port is a validation of the assay and indicates that no analyte is present in the fluid sample. No signal in the display port indicates the presence of analyte in the fluid sample.

The analytical test device allows the assay to be performed in a single step. The user only has to apply the fluid sample to the contacting surface, and then observe the results.

The analytical test device is assembled by placing the absorbent membrane and the reaction membrane on the bottom and then the top is then placed on the bottom to ensure a tight fit. One skilled in the art would understand that any suitable means to ensure a tight fit between the top and bottom can be used. For example, the top can be fitted on the bottom with snaps or glue.

Also, to ensure fluid retention, the analytical test device of the present invention is preferably made of a nonporous plastic, such as the commercially available plastic "ABS" supplied by the Monsanto Company of St. Louis, Mo. In an embodiment of the device, once a cap is placed over the contacting surface extending outward from the bottom, the device becomes substantially fluid-tight and evaporation of the fluid sample is minimized. This configuration also has the advantage of avoiding spillage and the need for any further contact between the sample and user.

Several features of the analytical test device assist in avoiding compromised results. First, the simultaneous migration of an excessive amount of fluid sample is limited by requiring the fluid sample to ascend through the absorbent membrane by capillary action, rather than applying the fluid sample to the absorbent membrane directly. Second, the spatial separation of the diffusively bound labeled reagent on the absorbent membrane from the point at which the fluid sample first contacts the absorbent membrane, ensures that the assay is not compromised by reagent leaking out into the fluid sample. Third, the impact of leading edge effects caused by depletion of bound reagents or labels, are minimized by physically separating the test and control regions, by applying the fluid sample evenly and at the same height across the absorbent membrane and by using the presence of a reaction, rather than the appearance of a given shape, (such as a "+" or a "−"), to signify a positive or negative result. In addition, the entire process is simplified by having the label bound to the absorbent membrane placed within the device, thus avoiding any need for the user to add a reagent or mix it with fluid sample.

As described above, the present invention is also ideally suited to the application of more than one fluid sample to a single analytical test device. In prior devices, such as the one described in May et al., U.S. Pat. No. 5,602,040, issued Feb. 11, 1997, the device (hereinafter the '040 device) is typically held in a stream of urine. The protruding sample aperture in the '040 device is in contact with the dry porous carrier inside the hollow casing of the device. Thus, the test proceeds immediately upon application of the sample. Therefore, such a device is suited for the testing of only one sample at a time.

Moreover, since the user of the '040 device typically holds the protruding bibulous member in the urine stream, the sample would likely be unevenly applied to the membrane. Thus, the '040 device suffers from leading edge effects created by an uneven solvent front along the membrane. Accordingly, the reagents and bound labels could be depleted and the results could be misleading. In contrast, the user of the present analytical test device is assured that the solvent front formed by the fluid sample will be uniform since the fluid sample contacts the absorbent membrane evenly and at the same height across the absorbent membrane. Therefore, the present analytical test device provides more reliable results.

As used herein, the terms "ligand" and "control reagents" are used interchangeably, and refer to a molecule to which another molecule will bind. A ligand or control reagent can be human, animal or plant in origin. For purposes of this invention, these may include LH, hCG or other naturally occurring biological ligands in serum, plasma, urine or other fluids and will preferably include analytes. Specifically, it will be appreciated by those skilled in the art that the ligand or control reagent or analyte may be a protein, peptide, amino acid, nucleic acid, sugar, hormone, steroid, vitamin, toxin in the sample fluid, pathogenic microorganism and metabolites from analogs of such analytes, or antibodies to these substances. They may also include hormones, haptens, immunoglobulin, polynucleotides, drugs and infectious disease agents (bacterial or viral) such as Streptoccus, Neisseria, Chlamydia, Gonorrhea and HIV.

As used herein, the term "reagent" refers to receptor molecules which bind to a ligand. Reagents may, in this context, include any naturally occurring or synthetic biological receptor and will preferably include antibodies. The antibodies may be polyclonal or monoclonal. For simplicity, the terms antibody and analyte will be used interchangeably with reagent and ligand, respectively, throughout this disclosure. It will be appreciated by those skilled in the art, however, that the invention is not limited to use with analytes and antibodies.

Ligand-reagent pairs useful in the present invention include specific binding pairs such as antigens and antibodies, or fragments of antibodies, both polyclonal and monoclonal, lectins and carbohydrates, hormones and hormone receptors, enzymes and enzyme substrates, biotin and avidin, vitamins and vitamin binding proteins, complementary polynucleotide sequences, drugs and receptors, enzymes and inhibitors, apoproteins and cofactors, growth factors and receptors, and the like. Biotin and avidin derivatives may also be used, including biotin analogs/avidin, biotin/streptavidin, and biotin analogs/streptavidin. Members of the complex may be "engineered," that is, made by synthetic means. Such techniques are well known in the art, and include techniques for chimeric and humanized antibodies and fragments thereof, synthetic peptides, and synthetic RNA and DNA oligonucleotides.

Any known reagent can be used in any known format such as, for example, sandwich and competitive binding formats, to specifically detect an analyte in a fluid sample. Examples of such reagents are those disclosed in: H. J. Friesen, U.S. Pat. No. 4,861,711, issued Aug. 29, 1989; J. Bunting, U.S. Pat. No. 4,271,140, issued Jun. 2, 1981; May et al., U.S. Pat. No. 5,622,871, issued Apr. 22, 1997; May et al., U.S. Pat. No. 5,656,503, issued Aug. 12, 1997; May et al., U.S. Pat. No. 5,602,040, issued Feb. 11, 1997; and R. Rosenstein, U.S. Pat. No. 5,591,645, issued Jan. 7, 1997 (each of which is incorporated by reference herein). Such reagents can form a detectable complex with such ligands as listed above.

Preferred reagents include antibodies to a hormone or infectious disease agent. Preferred antibodies include anti-hCG antibodies and anti-human LH antibodies, especially of the IgG class, and even more so murine monoclonal antibodies and especially those that have been affinity purified. One skilled in the art would recognize, however, that polyclonal antibodies could also be employed in the present invention.

By the term "non-diffusively bound" is meant covalent or non-covalent attachment to the membrane such that the advancing fluid sample does not cause movement of the non-diffusively bound reagent or non-diffusively bound control reagent from the place it is applied on the reaction membrane. Conversely, by the term "diffusively bound" is meant placement such that the advancing fluid sample does cause movement of the diffusively bound labeled reagent from the place it is applied on the absorbent membrane.

As used herein, the term "fluid sample" refers to a material suspected of containing an analyte. The fluid sample can be used directly as obtained, for example, from any biological source. The fluid sample can also be obtained from an organism and the relevant portion extracted or dissolved into a solution. For example, the fluid sample can be a physiological fluid, such as, for example, saliva, ocular lens fluid, cerebral spinal fluid, sweat, blood, pus, mucus, serum, urine, milk, ascites fluid, synovial fluid, peritoneal fluid, amniotic fluid, and the like. In addition, the fluid sample fluid can be extracted from throat swabs, feces, or from other biological samples.

As used herein, the term "label" refers to a molecule that directly or indirectly mediates the production of a signal (such as a color change) which is used in assay procedures to indicate the presence or absence of analyte in a fluid sample. Labels may include enzymes, fluorescent molecules and will preferably include metal sols. Labels include colored latex spheres and colloidal metals. Labels include those disclosed by D. Yost et al., U.S. Pat. No. 4,954,452, issued Sep. 4, 1990; J. Leuvering, U.S. Pat. No. 4,313,734, issued Feb. 2, 1982; P. Tarcha et al., U.S. Pat. No. 5,252,459, issued Oct. 12, 1993; T. Gribnau et al., U.S. Pat. No. 4,373,932, issued Feb. 15, 1983; and R. Campbell, U.S. Pat. No. 4,703,013, issued Oct. 27, 1987 (each of which is incorporated by reference herein).

Alternatively, the label can be colored latex particles (see Campbell, U.S. Pat. No. 4,703,017, issued Oct. 27, 1987, which is incorporated by reference herein) or can be an enzyme that has reacted with a colorless substrate to give a colored product and is encapsulated, for example, in a liposome (see E. Soini, U.S. Pat. No. 5,518,883, issued May 21, 1996, which is incorporated herein by reference). The label may also be an inducible property of the particles, such as colorable latex particles (see Gribnau et al., U.S. Pat. No. 4,373,932, issued Feb. 15, 1983, and de Jaeger et al., U.S. Pat. No. 4,837,168, issued Jun. 6, 1989, both of which are incorporated by reference herein).

Alternatively, the label can be fluorescent molecules, such as the rhodamine, fluorescein, or umbelliferone series, employed by themselves or with a quencher molecule (see, for example, Ullman et al., U.S. Pat. No. 3,996,345, issued Dec. 7, 1976 and Tom et al., U.S. Pat. No. 4,366,241, issued Dec. 28, 1982, both of which are incorporated herein by reference). Chemiluminescent molecules, such as luminol, luciferin, lucigenin, or oxalyl chloride can be used as a signal means (see, for example, Maier, U.S. Pat. No. 4,104,029, issued Aug. 1, 1978, which is incorporated herein by reference). Finally, enzymatic systems that react with a colorless substrate to give a colored product, such as horseradish peroxidase, alkaline phosphatase, indoxyl phosphate and aminoethylcarbazole may be used as labels.

Analytical test devices using labeled reagents are also provided in K. May, U.S. Pat. No. 5,656,503, issued Aug. 12, 1997. However, in those devices, the mobility of the labeled reagent is facilitated by using sugar in an amount effective to reduce interaction. Sugar is not used in the present invention to assist mobility of the labeled reagent.

Diffusively bound complexed antibodies can be impregnated into the immunoassay within the absorbent membrane. The diffusively bound complexed antibodies are located upstream from a zone on the reaction membrane of the immunoassay that contains immobilized antibodies. The diffusively bound label complexed antibodies bind to the analyte and are carried to the zone containing the immobilized antibodies where a sandwich antibody-hormone complex is formed and detected. However, if desired, both the diffusively bound and non-diffusively bound antibodies may be disposed on a single membrane.

In one embodiment, the diffusively bound labeled reagent will be labeled according to means known in the art. For purposes of producing a clearly visible reaction, labels of metal sols are preferred, with labels of colloidal gold or selenium being most preferred. An example of a suitable product is colloidal gold available from Janssen Life Sciences Products. These colloidal metals will produce colored reactions without addition of further reagents. However, fluorescent compounds (such as fluorescein and phycobiliprotein) and enzymes (such as those identified in U.S. Pat. No. 4,275,149, which is incorporated by reference herein), may also be used. To maximize contact of analyte with labeled reagent, the latter should be bound to the membrane across its face; i.e., from one side to the other (see, bar 354 shown in phantom on FIGS. 16, 17 and 18).

As used herein, the term "metal label" includes labels of metal sols; i.e., metal or metal compounds such as metal oxides, metal hydroxides, metal salts or polymer nuclei coated with a metal or metal compound. These metal labels may include dry forms of any of the above-named metals or metal compounds, and will preferably include colloidal gold in dry form. For example, the metal label can be composed of a metal sol, a selenium sol or a carbon sol (see, for example, Leuvering et al., U.S. Pat. No. 4,313,734, issued Feb. 2, 1982; Moremans et al., U.S. Pat. No. 4,775,636, issued Oct. 4, 1988; Yost et al., U.S. Pat. No. 4,954,452, issued Sep. 4, 1990; and Kang et al., U.S. Pat. No. 5,559,041, issued Sep. 24, 1996, each of which is incorporated by reference herein)

Depending on th e context in which it is used, "reaction complex" or "complex" shall mean a complex of analyte and diffusively bound labeled reagent complex first produced in the assay ("first complex"), a complex of first complex and the non-diffusively bound reagent produced second in the assay ("second complex"), or a complex of the second complex and the non-diffusively bound control reagent produced third in the assay ("third complex"). The complex can be made up of a ligand-reagent pair that has spatial and/or polar features which permit it to bind specifically to each other. By "first member" of the complex is meant the member bound, covalently or non-covalently, at least to a sub-population of the particles. The "second member" of a complex refers to the corresponding binding member of the pair non-diffusively bound in the control region.

As used herein, the term "sample aperture" refers to an opening on the top to which the fluid sample can be added by any means, such as for example, dropping or by pipette. Preferably, the sample aperture will be located on the top at a point over the contacting surface.

The term "entry port" refers to an aperture on the embodiment of the device containing the contacting surface extending outward from the bottom. The entry port allows fluid sample to enter the assembled top and bottom from the contacting surface.

The term "display port" refers to any means whereby visual access to the reaction membrane can be gained. In one embodiment, a display port will be an aperture in the top positioned over the reaction membrane. In another embodiment there will be two display ports. A display port also encompasses all or any part of the top made of a clear or transparent material so that the reaction membrane can be seen. Thus, if the entire top is made of clear or transparent material, then the entire top is the display port. In addition there may be a clear or transparent membrane placed between the reaction membrane and the aperture of the display port in order to prevent evaporation of fluid sample, to prevent fluid sample or other fluid from entering the display port, or to prevent contamination of the reaction membrane by touching, all of which can affect the performance of the assay.

The term "contacting surface" refers to a surface of the analytical test device that first contacts the fluid sample when the fluid sample is added. It is contemplated that the contacting surface could encompass, for example, a plane, a curved or bent plane, a groove or a channel. The contacting surface will be disposed at a descending angle to the slope. In the embodiment of the analytical test device containing the contacting surface extending outward from the bottom, the contacting surface will be attached at a descending angle to the slope and indirectly to the slope through the optional lower plane of the bottom. Here, the lower plane and upper plane are preferably parallel to one another and the contacting surface is not parallel to either the lower plane or the upper plane. In the embodiment of the analytical test device with the sample aperture on the top, the contacting surface can be the attached to the slope directly and will be directly beneath the sample aperture. In this embodiment, the contacting surface, preferably, will not be parallel to the upper plane.

As used herein, the term "descending angle" refers to any angle, other than 180°, between the contacting surface and the upper plane. Thus, it is contemplated that the contacting surface will not be parallel to either the lower plane or upper plane of the bottom of the analytical test device. Also preferably, fluid sample contacted with the contacting surface should run into the absorbent membrane with the aid of gravity. However, tilting the device can control movement of the fluid sample.

The terms "absorbent membrane" and "reaction membrane" refer to any bibulous, porous or fibrous material capable of rapidly absorbing an aqueous fluid and conducting the fluid via capillary attraction. Suitable materials are described, for example, in H. J. Friesen, U.S. Pat. No. 4,861,711, issued Aug. 29, 1989; J. Bunting, U.S. Pat. No. 4,271,140, issued Jun. 2, 1981; May et al., U.S. Pat. No. 5,622,871, issued Apr. 22, 1997; May et al., U.S. Pat. No. 5,656,503, issued Aug. 12, 1997; May et al., U.S. Pat. No. 5,602,040, issued Feb. 11, 1997; and R. Rosenstein, U.S. Pat. No. 5,591,645, issued Jan. 7, 1997 (each of which is incorporated by reference herein). The preferred material for the absorbent membrane is a fiberglass product such as that marketed as "MANNIWEB" or "MANNIGLAS" by Lydall, Inc., Manchester, Conn. Other suitable materials include polyethylene or nitrocellulose pads and strips. The means for binding reagents to these materials are well-known in the art. Preferred materials include nitrocellulose, nylon, paper and silica gel. An advantage of a nitrocellulose membrane is that an immobilized antibody described above can be attached without prior chemical treatment. However, antibodies can be immobilized on other materials such as filter paper using well known chemical coupling methods such as, for example, CNBr, carbonyldimidazole or tresyl chloride. The reaction membrane will preferably be a chromatographic strip coated with gelatin to enhance the life of the strip and clarity of any visible reactions produced in the test.

The present invention also provides methods of using the analytical test device for detecting an analyte in a fluid sample, comprising contacting the fluid sample to the contacting surface and observing the reaction complex through the display port. Also preferably, the analytical test device will have a first display port and a second display port, and preferably, the reaction complex will be visible.

Figure 1:
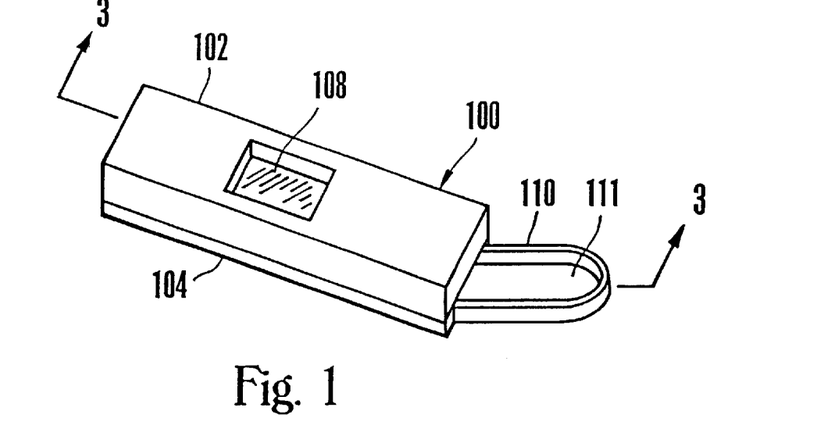
FIG. 1 is a perspective view of an analytical test device containing a contacting surface extending outward from the bottom.

FIG. 1 shows a perspective view of one embodiment of an analytical test device for performing assays in accord with the invention. Although any appropriate shape may be employed, FIG. 1 depicts housing 100 of rectangular shape. Housing 100 has top 102, in which one opening appears, and bottom 104. The opening through top 102 is a display port 108 through which the test result can be viewed and compared.

On an end of bottom 104 is protruding sample well 110 and contacting surface 111. Although FIG. 2 shows the protruding sample well 110 and the contacting surface 111 pointed slightly upward at an oblique angle to the end of the housing, it is understood that the protruding sample well 110 or the contacting surface 111 can be placed at any other angle in relation to upper plane 122, other than 180°.

Figure 2:
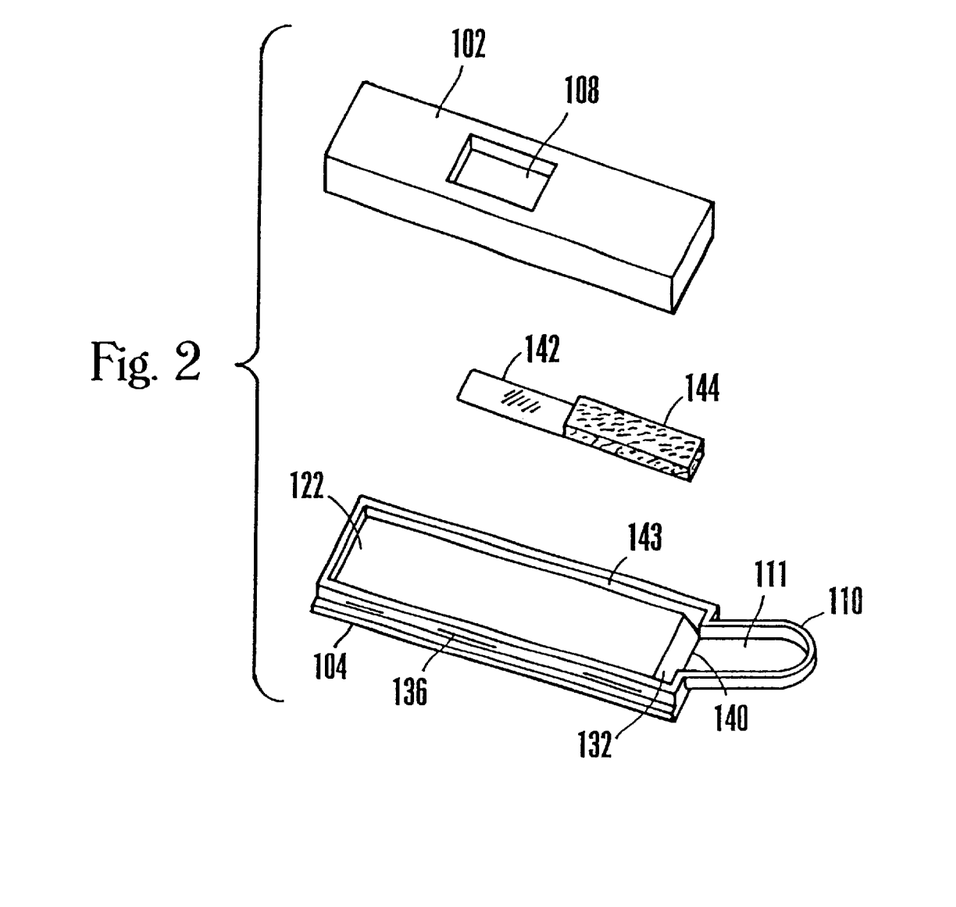
FIG. 2 is an exploded view showing the components of the analytical test device of FIG. 1.

FIG. 2 shows an exploded view of the analytical test device of FIG. 1. In this view, it can be seen that bottom 104 has sidewalls 143, snaps 136, upper plane 122 and slope 132. Entry port 140 is located between slope 132 and contacting surface 111.

As seen in FIG. 2, contained within housing 100 (as depicted in corresponding inexploded FIG. 1) will be absorbant membrane 144 and reaction membrane 142 containing the reagents to detect an analyte in a fluid sample.

Absorbent membrane 144 will be disposed along slope 132 to upper plane 122. Reaction membrane 142 will be disposed along upper plane 122. Absorbent membrane 144 and reaction membrane 142 will be in contact with, but need not be affixed, to each other.

Figure 3:
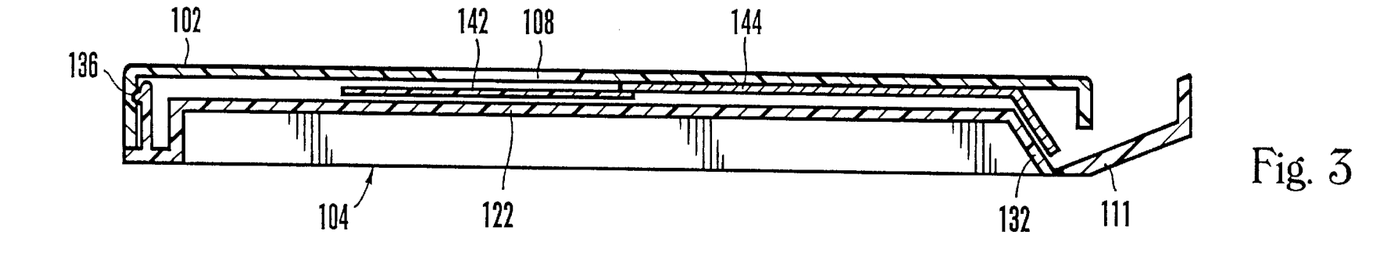
FIG. 3 is an enlarged sectional view along line 3—3 of the analytical test device of FIG. 1.

FIG. 3 is an enlarged sectional view of the analytical test device shown in FIG. 1. In this view the orientation of contacting surface 111 can be seen.

Figure 4:
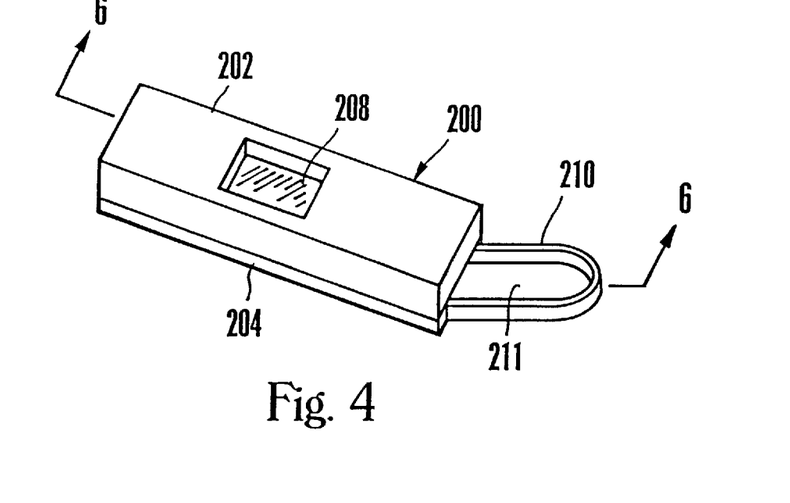
FIG. 4 is a perspective view of an embodiment of the analytical test device with a contacting surface extending outward from the bottom.

FIG. 4 shows a perspective view of an embodiment of the analytical test device shown in FIG. 1. To that end, housing 200 is composed of top 202, bottom 204 and has display port 208 positioned on top 202. On an end of bottom 204 is protruding sample well 210 and contacting surface 211. In addition, snaps 236 are shown.

Figure 5:
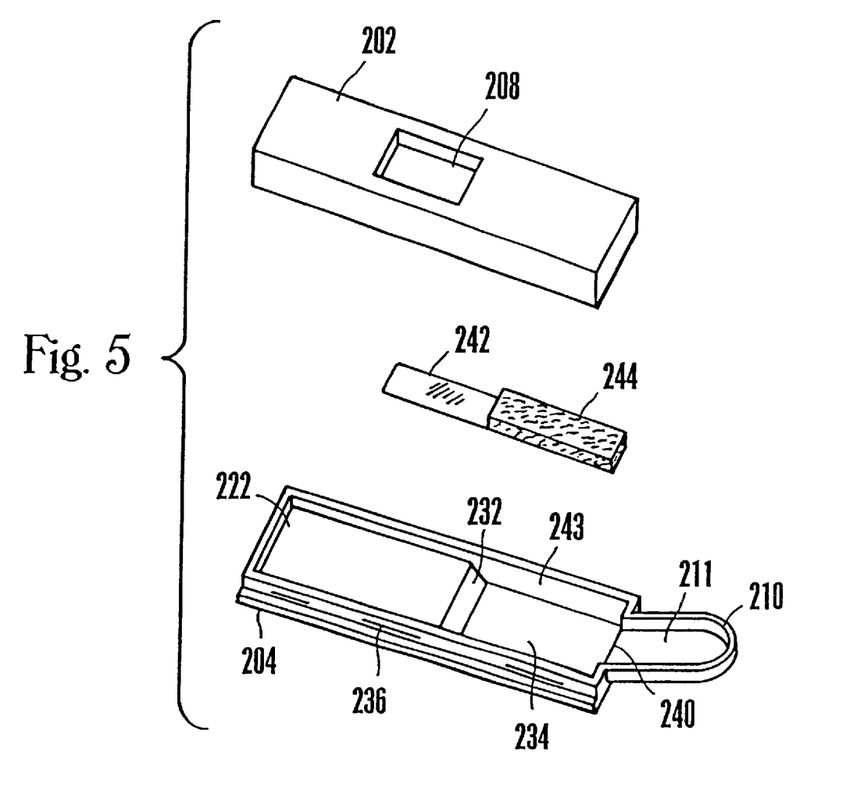
FIG. 5 is an exploded view showing the components of the analytical test device of FIG. 4.

FIG. 5 is an exploded view of the analytical test device shown in FIG. 4 and shows the components, bottom 204, contacting surface 211, sidewalls 243, lower plane 234, slope 232 and upper plane 222. It can be seen that contained within housing 200 (as depicted in corresponding inexploded FIG. 4) is absorbent membrane 244 and reaction membrane 242. Absorbent membrane 244 will be placed along lower plane 234 and along slope 232. Absorbent membrane 244 and reaction membrane 242 will be in contact with, but need not be affixed to each other.

Figure 6:
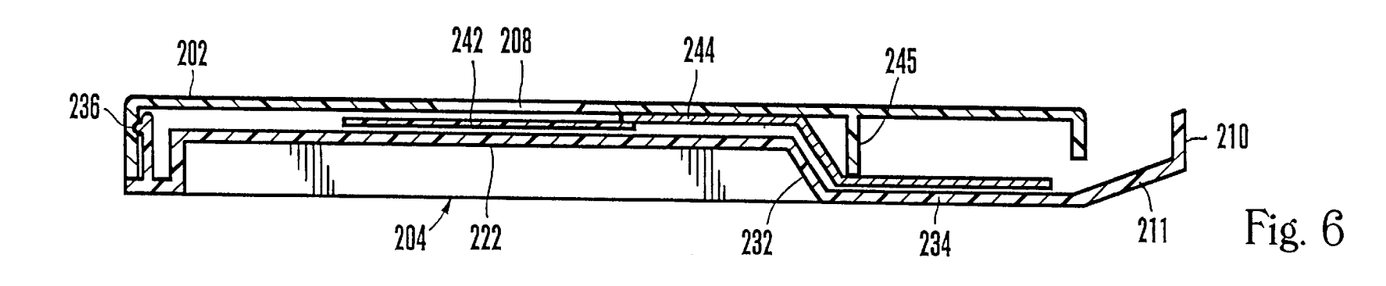
FIG. 6 is an enlarged sectional view along line 6—6 of the analytical test device of FIG. 4.

FIG. 6 is an enlarged sectional view of the analytical test device shown in FIG. 4. In this view, the orientation of protruding sample well 210 and contacting surface 211 can be seen. In addition, vertical bar 245 is present to hold absorbent membrane 244 down to follow the contour of slope 232.

Figure 7:
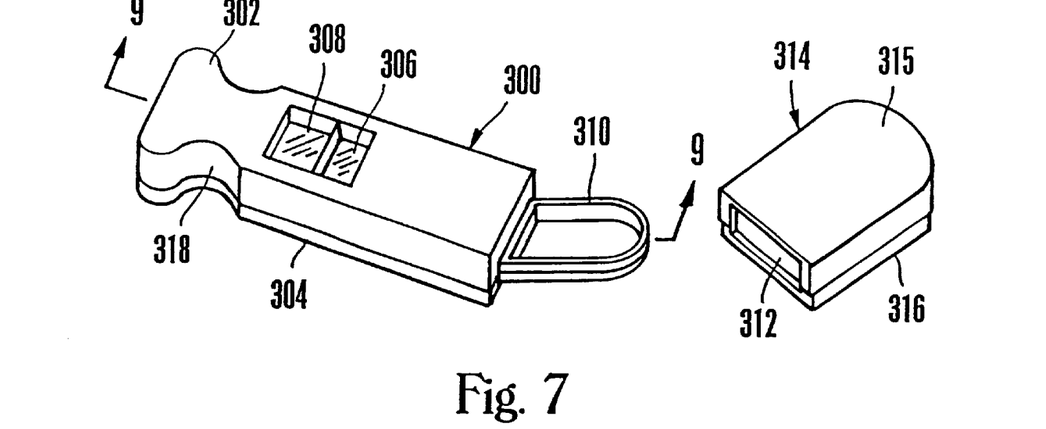
FIG. 7 is a perspective view of another embodiment of the analytical test device with a contacting surface extending outward from the bottom and a cap.

FIG. 7 shows a perspective view of another embodiment of an analytical test device for performing assays in accord with the invention. Top 302 has two openings forming first display port 306 and second display port 308, which are preferably in close proximity for ease of comparison of results. In addition, housing 300 has handle 318 for the convenience of the user. Also, cap 314 can be placed over protruding sample well 310. Cap 314 can be formed from a single piece or, preferably, a top 315 and a bottom 316. Orifice 312 allows cap 314 to fit over protruding sample well 310.

Figure 8:
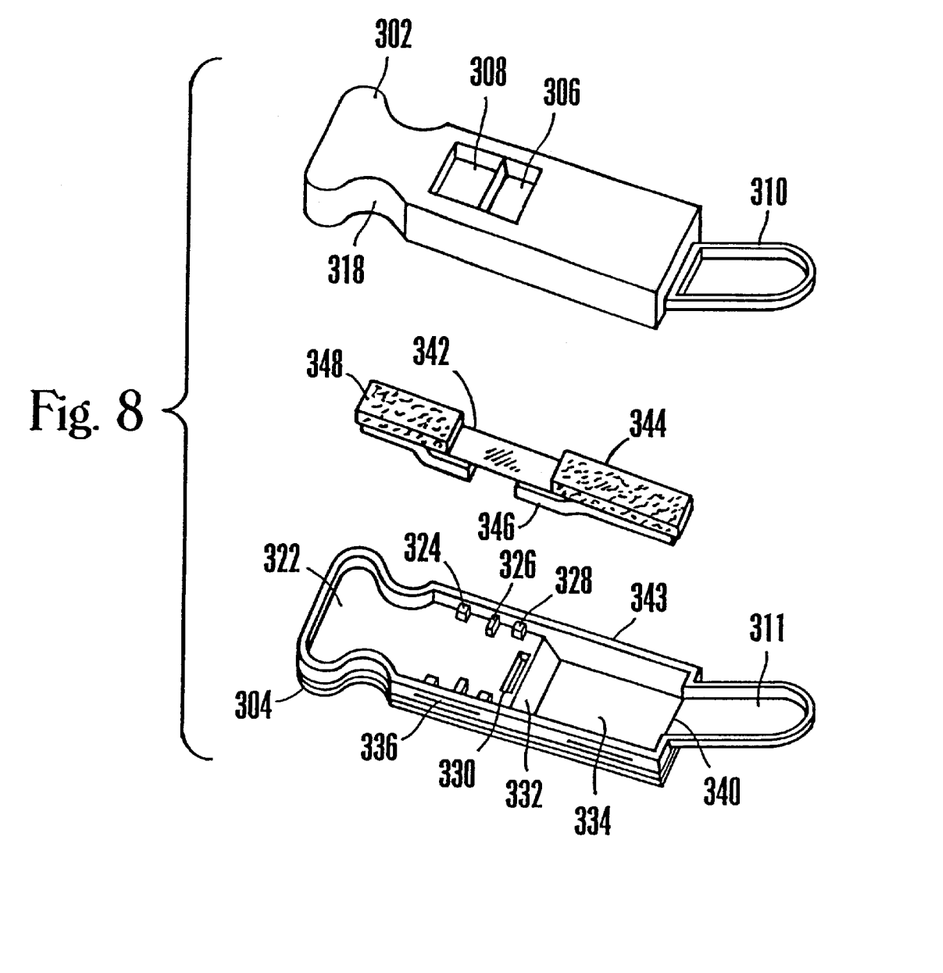
FIG. 8 is an exploded view showing the components of the analytical test device of FIG. 7.

FIG. 8 is an exploded view of the analytical test device shown in FIG. 7 and shows the components bottom 304, contacting surface 311, sidewalls 343, snaps 336, lower plane 334 slope 332, upper plane 322, fluid gully 330 and locating points 324, 326 and 328. It can be seen that contained within housing 300 (as depicted in corresponding inexploded FIG. 7) is absorbent membrane 344, reaction membrane 342 and collecting pad 348. Absorbent membrane 344 will be placed along lower plane 334 and along slope 332. Preferably, absorbent membrane 344 will be affixed to a nonporous substrate 346, such as vinyl or plastic coated paper by an adhesive or other means. Substrate 346 will extend along upper plane 322 to form a surface to which reaction membrane 342 will be affixed. Absorbent membrane 344 and reaction membrane 342 will be in contact with, but need not be affixed to each other. In another embodiment, absorbent membrane 344 will be split at its point of attachment to substrate 346 to extend above and below the substrate. This configuration serves to regulate the flow of fluid sample from absorbent membrane 344 to reaction membrane 342. Flow control can also be enhanced by placement of a well or fluid gully 330 below the junction between absorbent membrane 344 and reaction membrane 342.

Figure 9:
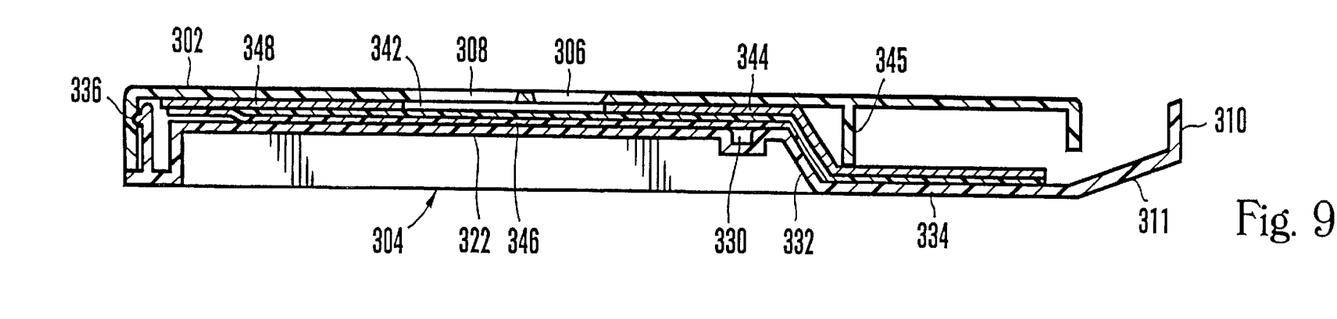
FIG. 9 is an enlarged sectional view along line 9—9 of the analytical test device of FIG. 7.

FIG. 9 is an enlarged sectional view of the analytical test device shown in FIG. 7. In this view the orientation of protruding sample well 310 and contacting surface 311 can be seen. In addition, vertical bar 345 is present to hold absorbent membrane 344 down to follow the contour of slope 332.

Figure 10:
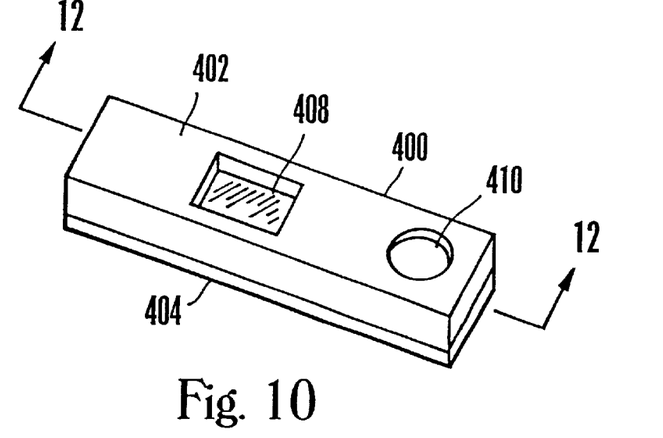
FIG. 10 is a perspective view of another embodiment of the analytical test device with a sample aperture on the top.

FIG. 10 is a perspective view of another embodiment of analytical test device with a sample aperture 410 on the top 402 of housing 400. In this embodiment, housing 400 is composed of top 402 and bottom 404. Top 402 contains display port 408.

Figure 11:
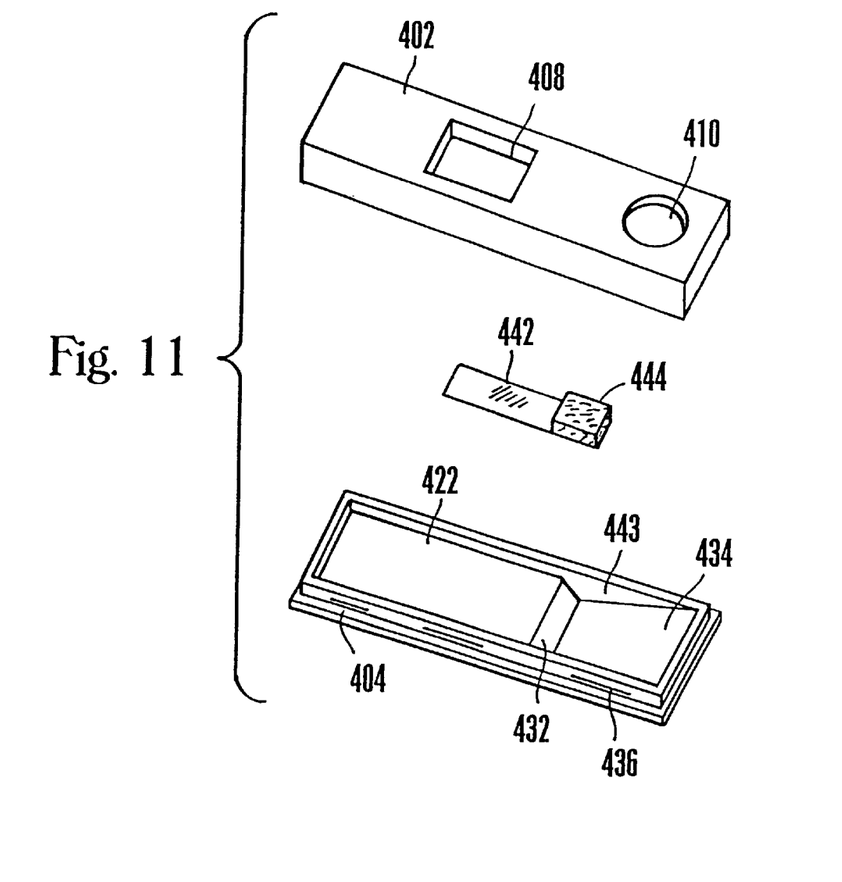
FIG. 11 is an exploded view showing the components of the analytical test device of FIG. 10.

FIG. 11 is an exploded view of the analytical test device of FIG. 10 and shows the components, bottom 404, contacting surface 434, sidewalls 443, snaps 436, slope 432, upper plane 422, and membranes containing the reagents for carrying out the assay, as described below. Contacting surface 434 is at a descending angle to slope 432. In this embodiment, absorbent membrane 444 is not disposed on contacting surface 434.

As seen in FIG. 11, contained within housing 400 (as depicted in corresponding inexploede FIG. 10) will be membranes containing the reagents necessary for carrying out the assay. In another embodiment there will be an absorbent membrane 444 and a reaction membrane 442.

Absorbent membrane 444 will be disposed along slope 432 to upper plane 422. Reaction membrane 442 will be disposed along upper plane 422. Absorbent membrane 444 and reaction membrane 442 will be in contact with, but need not be affixed, to each other.

Figure 12:
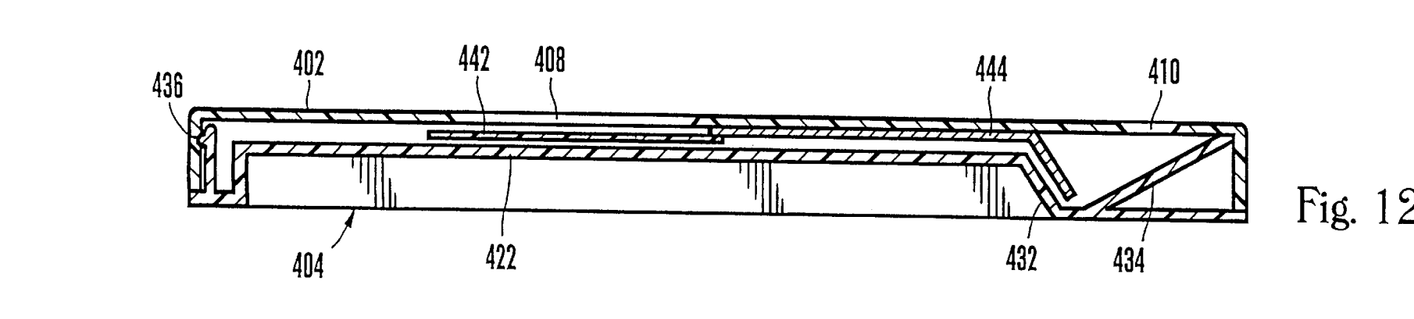
FIG. 12 is an enlarged-sectional view along line 12—12 of the analytical test device of FIG. 10.

FIG. 12 is an enlarged sectional view of the analytical test device shown in FIG. 10. The orientation of contacting surface 434 can be seen.

Figure 13:
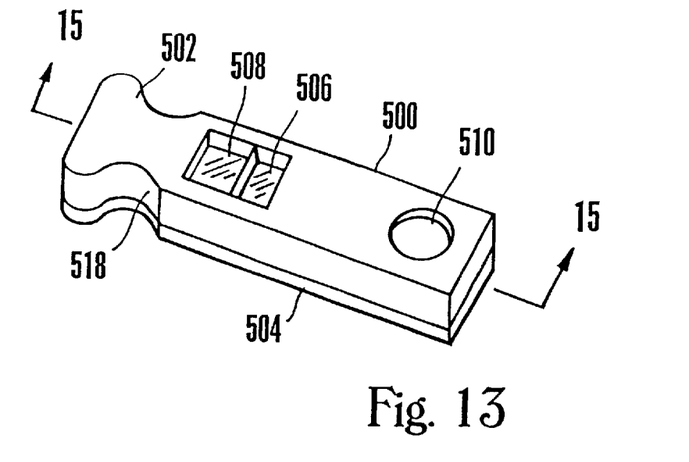
FIG. 13 is a perspective view of an embodiment of the analytical test device with a sample aperture on the top.

FIG. 13 shows a perspective view of an embodiment of the analytical test device shown in FIG. 10. In this embodiment, housing 500 is composed of top 502 and bottom 504. In addition, housing 500 has handle 518 for the convenience of the user. Top 502 contains a first display port 506 and a second display port 508 that are preferably in close proximity for ease of comparison of results.

Figure 14:
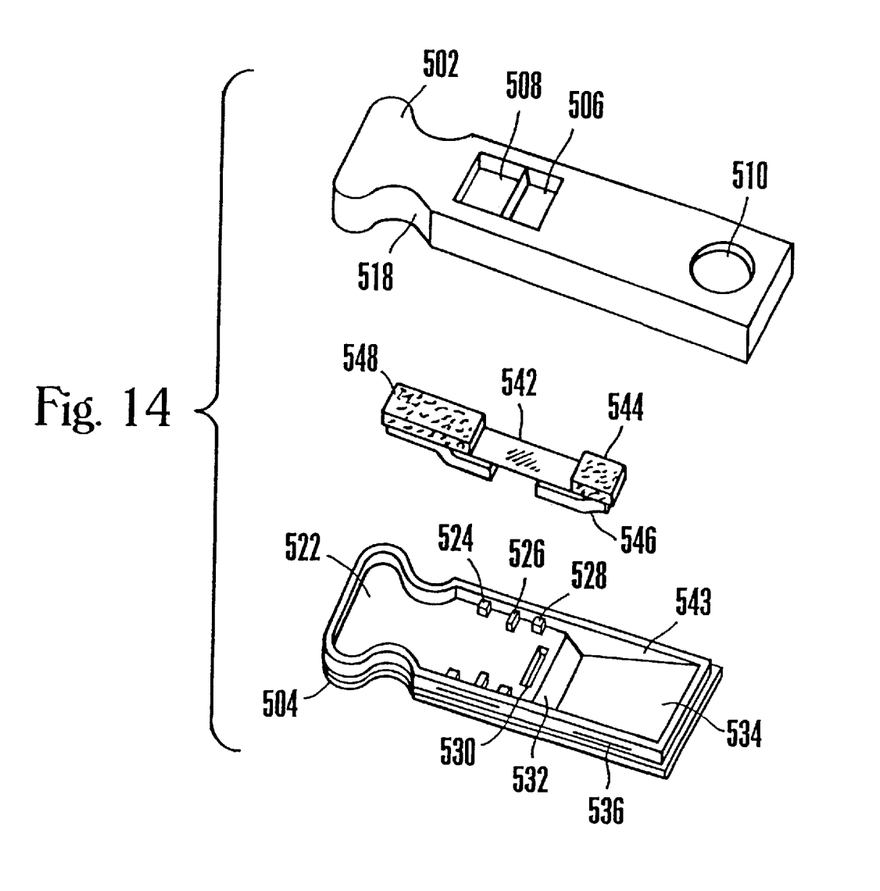
FIG. 14 is an exploded view showing the components of the analytical test device of FIG. 13.

FIG. 14 is an exploded view of the analytical test device shown in FIG. 13 and shows the components, bottom 504, contacting surface 534, sidewalls 543, snaps 536, slope 532, upper plane 522, fluid gully 530 and locating points 524, 526 and 528, and one or more membranes containing the reagents for carrying out the assay, as described below. To that end it can be seen that contained within housing 500 (as depicted in corresponding inexploded view in FIG. 13) is absorbent membrane 544, reaction membrane 542 and collecting pad 548. Absorbent membrane 544 will be placed along slope 532. Preferably, absorbent membrane 544 will be affixed to a nonporous substrate 546 such as vinyl coated paper or plastic coated paper by an adhesive or other suitable means. Substrate 546 will extend along upper plane 522 to form a surface to which reaction membrane 542 will be affixed. Absorbent membrane 544 and reaction membrane 542 will be in contact with, but need not be affixed to each other. In another embodiment, absorbent membrane 544 will be split at its point of attachment to substrate 546 to extend above and below the substrate. This configuration serves to regulate the flow of fluid sample from absorbent membrane 544 to reaction membrane 542. Flow control can also be enhanced by placement of a well or fluid gully 530 below the junction between membranes 544 and 542.

Figure 15:
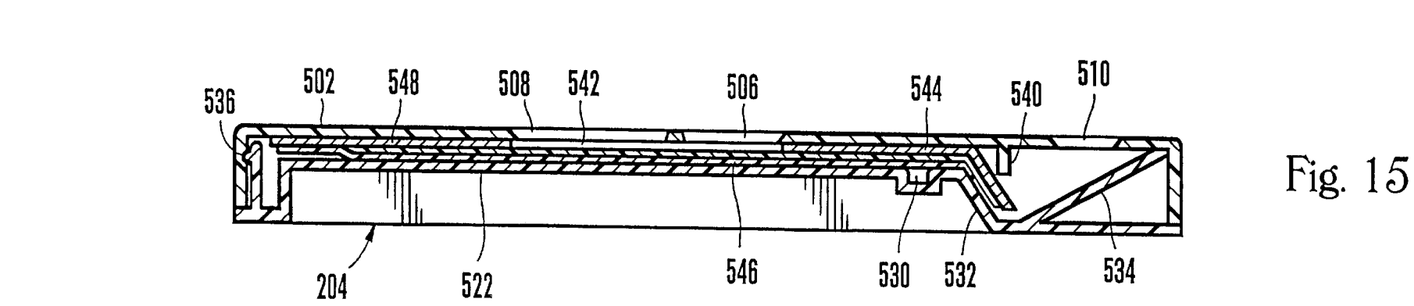
FIG. 15 is an enlarged sectional view along line 15—15 of the analytical test device of FIG. 13.

FIG. 15 is an enlarged sectional view of the analytical test device shown in FIG. 13. The orientation of contacting surface 534 can be seen. In addition, vertical bar 540 serves to hold absorbent membrane 544 down to follow the contour of slope 532.

Figure 16:
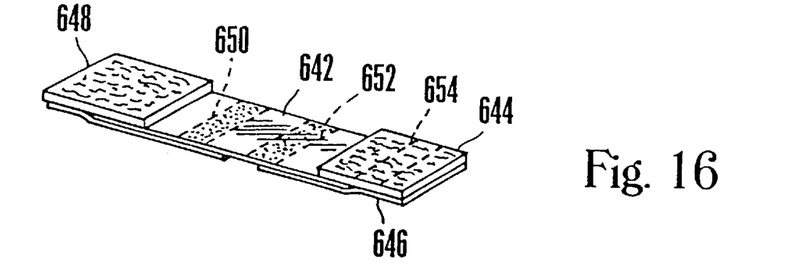
FIG. 16 is a perspective view of the absorbent and reaction membranes of the analytical test device employing a sandwich assay system showing a positive assay result.
Figure 17:
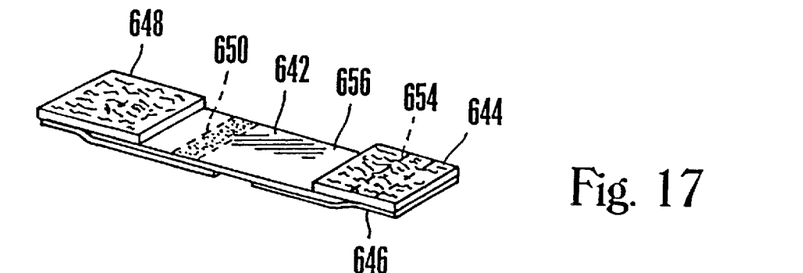
FIG. 17 is a perspective view of the absorbent and reaction membranes of the analytical test device employing a sandwich assay system showing a negative assay result.
Figure 18:
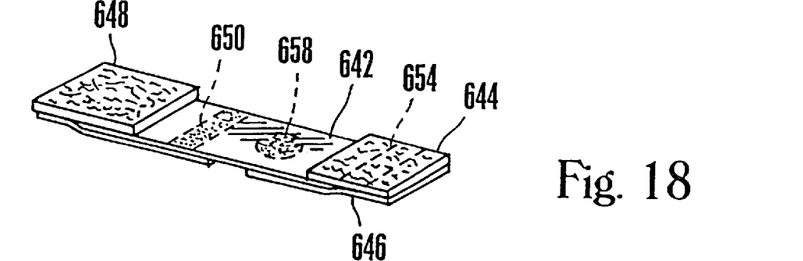
FIG. 18 is a perspective view of the absorbent and reaction membranes of the analytical test device employing a sandwich assay system showing an inconclusive assay result.

In FIGS. 16, 17, 18, 19 and 20 at point 654 on absorbent membrane 644 a diffusively bound labeled reagent, preferably an antibody and, most preferably an antibody to hCG, will be bound so as to be spatially separated from where the fluid sample first contacts the absorbent membrane. In FIGS. 16, 17 and 18, analyte in the fluid sample, if present, will bind to the diffusively bound labeled reagent at point 654 on the absorbent membrane 644 to form a first complex. If desired, further fluid sample may be added up to the maximum binding capacity of unlabeled reagent. The first complex and uncomplexed diffusively bound labeled reagent, if any, will be carried along with the fluid sample by capillary action ("wicking") up to the reaction membrane 642. The position of the diffusively bound labeled reagent and first complex, if any is indicated as 654 on FIGS. 16, 17 and 18. Substrate 646 is also shown.

All first complexes carried with the fluid sample will contact the reaction membrane 642. Fluid sample will pass through the reaction membrane 642, bringing the first complex, if any, into contact with the non-diffusively bound reagent to form a second complex composed of first complex/non-diffusively bound reagent. If second complexes are formed, they will appear in the test region at bar 652 (FIG. 16).

Fluid sample will continue its migration by wicking through reaction membrane 642 past the non-diffusively bound reagent to the non-diffusively bound control reagent. Diffusively bound labeled reagent not complexed to analyte will bind with the non-diffusively bound control reagent to form a third complex. The third complex will appear in the control region where bar 650 is shown (FIGS. 16, 17 and 18). Excess fluid sample will continue migrating to collecting pad 648.

Formation of all complexes in the assay method may be by sandwich or competitive immunoassay techniques well known to those skilled in the art. Within a predetermined time period, any second complex present and the third complex will produce a detectable signal mediated by the label. In another embodiment, the reaction complex will be a detectable a color change. This color change will signal either a positive (analyte present) or negative (analyte not present) reaction by providing two separate reactive regions within those portions of reaction membrane visible to the user through the display ports. Other control or comparative result signals may be provided, including signals that indicate whether an invalid result is obtained, by similar means known to those skilled in the art (see, for example, the signal system described in Brown et al., U.S. Pat. No. 5,160,701, issued Nov. 3, 1992, which is incorporated by reference herein).

As shown in FIG. 16, a positive result is indicated when color changes forming substantially similar shapes (in this instance, horizontal bars 650 and 652) appear. In contrast, as shown in FIG. 17, a negative result is indicated when a color change forming a distinguishable shape only appears, for example, as a horizontal bar 650. Finally, an inconclusive result is shown in FIG. 18, where color changes appear in both regions having substantially dissimilar shapes (i.e., horizontal bar 650 and smudge 658). In this latter instance, the user would be alerted that the test should be repeated. While due to the decreased impact of leading edge effects and similar phenomena in this assay it is not expected that inconclusive results will be frequent, the assay requires such a small application of fluid sample that repetition should not be problematic in most applications.

Figure 19:
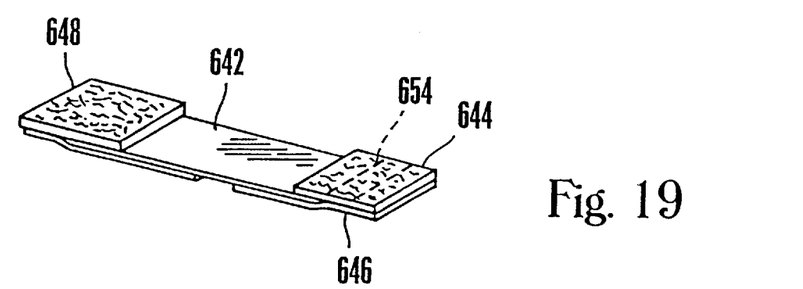
FIG. 19 is a perspective view of the absorbent and reaction membranes of an embodiment of the analytical test device employing a competitive assay system showing a positive assay result.
Figure 20:
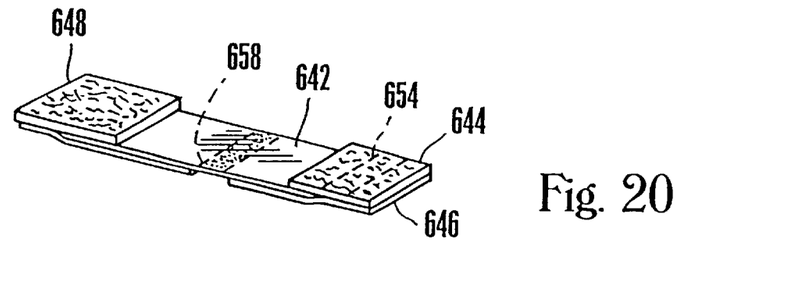
FIG. 20 is a perspective view of the absorbent and reaction membranes of an embodiment of the analytical test device employing a competitive assay system showing a negative assay result.

FIG. 19 and FIG. 20 show perspective views of absorbent membrane 644, reaction membrane 642 and the optional collecting pad 648, along with substrate 646, wherein a competitive assay is employed. FIG. 19 shows a positive assay result, as indicated by no signal in reaction membrane 642. FIG. 20 shows a negative assay result as indicated by the appearance of bar 658 in reaction membrane 642.

EXAMPLE I

Analytical Test Device with Contacting Surface Extending Outward from the Bottom This example describes the method and analytical test device depicted in FIG. 7 containing the contacting surface extending outward from the bottom.

The assay procedure is performed using anti-hCG antibody to form the second complex and an anti-hCG-colloidal gold compound to form the first complex. A fluid sample can be collected at any time of day, but for best results, it is best to test the first urine of the morning because it contains the highest concentration of hCG. The fluid sample is at least 1 cubic centimeter (hereinafter "cc") of urine suspected of containing hCG; the assay is performed at ambient temperatures not below 15° C. or exceeding 30° C. The 1 cc of urine is added to protruding sample well 310 by pipette. The fluid sample contacts contacting surface 311. The analytical test device is then tilted so that fluid sample enters entry port 340 and contacts absorbent membrane 344. Within 3 minutes visible color changes, (from pure white to pink) through substantially the center of display ports 306 and 308 on reaction membrane 342, are faintly visible. By the end of five minutes, a vividly pink bar symbol has appeared through substantially the center of each display port, indicating the presence of hCG in the sample. All other visible areas of the reaction membrane visible through the second display port remain white, which is the normally visible color of the reaction membrane. This assay may be performed at any time after a suspected conception to determine the presence of hCG and, therefore, pregnancy.

EXAMPLE II

Analytical Test Device with Sample Aperture on the Top

This example describes the method and analytical test device depicted in FIG. 13 containing a sample aperture on the top.

The assay procedure is performed using anti-hCG antibody to form the second complex and an anti-hCG-colloidal gold compound to form the first complex. A fluid sample can be collected at any time of day, but for best results, it is best to test the first urine of the morning because it contains the highest concentration of hCG. The fluid sample is at least 1 cubic centimeter (hereinafter "cc") of urine suspected of containing hCG; the assay is performed at ambient temperatures not below 15° C. or exceeding 30° C. The 1 cc of urine is added to the sample aperture 510 on the top by pipette. The fluid sample contacts contacting surface 534. The analytical test device is then fitted so that fluid sample contacts absorbent membrane 544 located at slope 532. Within 3 minutes visible color changes, (from pure white to pink) through substantially the center of display ports 506 and 508 on reaction membrane 542, are faintly visible. By the end of five minutes, a vividly pink bar symbol has appeared through substantially the center of each display port, indicating the presence of hCG in the sample. All other visible areas of the reaction membrane visible through the second display port remain white, which is the normally visible color of the reaction membrane. This assay may be performed at any time after a suspected conception to determine the presence of hCG and, therefore, pregnancy.

Although the invention has been described with reference to the examples provided above, it should be understood that various modifications can be made without departing from the spirit of the invention. Accordingly, the invention is limited only by the claims.

I claim:

1. An analytical test device having a front and a back, comprising:
   (a) a top element having a display port;
   (b) a bottom element comprising a descending contacting surface in front, an upper plane in back and an interposed ascending slope,
      wherein the lower end of the descending contacting surface is connected to the lower end of the ascending slope and the upper end of the ascending slope is attached to the upper plane; and
   (c) a strip sandwiched between the top and bottom elements comprising, in fluid communication, an absorbent membrane in the front and a reaction membrane in the back having one or more reagents that form a reaction complex with an analyte in a fluid sample;
   wherein the reaction membrane is visible through the display port and the absorbent membrane extends along at least the upper end of the slope.

2. The analytical test device of claim 1, wherein the top element and bottom element further form a sample entry port and the contacting surface extends outward from the bottom element and the absorbent membrane is in fluid flow contact with the contacting surface through the entry port.

3. The analytical test device of claim 1, wherein the top element further comprises a vertical bar directed toward the bottom element that deflects the absorbent membrane to follow the contour of the slope.

4. The analytical test device of claim 1, wherein the bottom element further comprises a lower plane interposed between the lower end of the slope and the lower end of the contacting surface.

5. The analytical test device of claim 1, further comprising a cap placed over the contacting surface.

6. The analytical test device of claim 1, further comprising a collecting pad in fluid flow contact with the back end of the reaction membrane.

7. The analytical test device of claim 1, wherein the top element further has a sample aperture and the contacting surface is below the sample aperture.

8. The analytical test device of claim 1, wherein one reagent is a labeled reagent capable of migrating with the sample and is deposited on the absorbent membrane at a downstream point spatially separated from an upstream point where the fluid sample first contacts the absorbent membrane.

9. The analytical test device of claim 8, further comprising
   (a) a second reagent, complementary to an analyte in the fluid sample, immobilized to the reaction membrane at a first point beneath the display port; and
   (b) a control reagent, complementary to the labeled reagent, immobilized to the reaction membrane at a second point beneath the display port, wherein the first and second points are spatially separated.

10. The analytical test device of claim 9, wherein the top element comprises a first display port and a second display port, wherein the second reagent is positioned beneath the first display port and the control reagent is positioned beneath the second display port.

11. The analytical test device of claim 8, further comprising a second reagent that is immobilized to the reaction membrane beneath the display port, wherein the analyte and the labeled reagent compete for binding to the second reagent, or wherein the second reagent and the analyte compete for binding to the labeled reagent.

12. A method for detecting an analyte in a fluid sample, comprising the steps of:
   (a) contacting the fluid sample to the contacting surface of the analytical test device of claim 1; and
   (b) detecting the analyte by observing the presence of a reaction complex on the reaction membrane through the display port.

13. The method of claim 12, wherein the presence of reaction complex is visible.

14. The analytical test device of claim 1, whereby when the fluid sample is applied to the contacting surface, the sample runs down the contacting surface and builds up from the lower end of the slope to the upper end until the sample comes into fluid flow contact with the absorbent membrane in an even fluid front.

* * * * *